US010582860B2

(12) United States Patent
Gregorich et al.

(10) Patent No.: US 10,582,860 B2
(45) Date of Patent: Mar. 10, 2020

(54) PRESSURE-SENSING MEDICAL DEVICES AND MEDICAL DEVICE SYSTEMS

(71) Applicant: BOSTON SCIENTIFIC SCIMED, INC., Maple Grove, MN (US)

(72) Inventors: Daniel J. Gregorich, Plymouth, MN (US); Roger W. McGowan, Ostego, MN (US); Michael J. Tierney, Pleasanton, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1185 days.

(21) Appl. No.: 14/011,322

(22) Filed: Aug. 27, 2013

(65) Prior Publication Data

US 2014/0058275 A1    Feb. 27, 2014

Related U.S. Application Data

(60) Provisional application No. 61/693,625, filed on Aug. 27, 2012.

(51) Int. Cl.
| | |
|---|---|
| *A61B 5/021* | (2006.01) |
| *A61B 5/0215* | (2006.01) |
| *A61M 25/00* | (2006.01) |
| *A61M 25/09* | (2006.01) |

(52) U.S. Cl.
CPC ...... *A61B 5/02141* (2013.01); *A61B 5/02154* (2013.01); *A61B 5/02156* (2013.01); *A61M 25/09* (2013.01); *A61M 2025/0002* (2013.01); *A61M 2025/09183* (2013.01)

(58) Field of Classification Search
CPC .................................................. A61B 5/0215
See application file for complete search history.

(56) References Cited

U.S. PATENT DOCUMENTS

| | | | |
|---|---|---|---|
| 3,963,323 | A | 6/1976 | Arnold |
| 4,771,782 | A | 9/1988 | Millar |
| 4,953,553 | A | 9/1990 | Tremulis |
| 5,106,455 | A | 4/1992 | Jacobsen et al. |
| 5,178,159 | A | 1/1993 | Christian |
| 5,238,004 | A | 8/1993 | Sahatjian et al. |
| 5,313,957 | A | 5/1994 | Little |
| 5,421,195 | A | 6/1995 | Wlodarczyk |

(Continued)

FOREIGN PATENT DOCUMENTS

| | | |
|---|---|---|
| CN | 102202562 A | 9/2011 |
| CN | 102469943 A | 5/2012 |

(Continued)

*Primary Examiner* — Jacqueline Cheng
*Assistant Examiner* — Tho Q Tran
(74) *Attorney, Agent, or Firm* — Seager, Tufte & Wickhem, LLP

(57) ABSTRACT

Medical device systems and methods for making and using medical device systems are disclosed. An example medical device system may include a guidewire. A pressure sensor assembly may be disposed within the guidewire. The pressure sensor assembly may include a pressure sensor and a first optical fiber coupled to the pressure sensor. The first optical fiber may have a first outer diameter. A cable may be coupled to the guidewire. The cable may include a second optical fiber. The second optical fiber may have a second outer diameter greater than the first outer diameter.

14 Claims, 13 Drawing Sheets

(56) References Cited

U.S. PATENT DOCUMENTS

| | | | |
|---|---|---|---|
| 5,422,969 A | 6/1995 | Eno | |
| 5,427,114 A | 6/1995 | Colliver et al. | |
| 5,438,873 A | 8/1995 | Wlodarczyk et al. | |
| 5,573,520 A | 11/1996 | Schwartz et al. | |
| 5,633,963 A | 5/1997 | Rickenbach et al. | |
| 5,748,819 A * | 5/1998 | Szentesi | G02B 6/2551 385/60 |
| 5,755,668 A | 5/1998 | Itoigawa et al. | |
| 5,772,609 A | 6/1998 | Nguyen et al. | |
| 5,797,856 A | 8/1998 | Frisbie et al. | |
| 5,872,879 A | 2/1999 | Hamm | |
| 5,902,248 A | 5/1999 | Millar et al. | |
| 5,938,624 A | 8/1999 | Akerfeldt et al. | |
| 5,949,929 A | 9/1999 | Hamm | |
| 5,987,995 A * | 11/1999 | Sawatari | A61B 5/0215 600/480 |
| 6,112,598 A | 9/2000 | Tenerz et al. | |
| 6,120,457 A | 9/2000 | Coombes et al. | |
| 6,139,510 A | 10/2000 | Palermo et al. | |
| 6,162,182 A | 12/2000 | Cole | |
| 6,167,763 B1 | 1/2001 | Tenerz et al. | |
| 6,196,980 B1 | 3/2001 | Akerfeldt et al. | |
| 6,248,083 B1 | 6/2001 | Smith et al. | |
| 6,265,792 B1 | 7/2001 | Granchukoff | |
| 6,394,986 B1 | 5/2002 | Millar | |
| 6,398,738 B1 | 6/2002 | Millar | |
| 6,409,677 B1 | 6/2002 | Tulkki | |
| 6,428,336 B1 | 8/2002 | Akerfeldt | |
| 6,508,803 B1 | 1/2003 | Horikawa et al. | |
| 6,565,514 B2 | 5/2003 | Svanerudh et al. | |
| 6,579,246 B2 | 6/2003 | Jacobsen et al. | |
| 6,585,660 B2 | 7/2003 | Dorando et al. | |
| 6,615,067 B2 | 9/2003 | Hoek et al. | |
| 6,663,570 B2 | 12/2003 | Mott et al. | |
| 6,666,591 B2 * | 12/2003 | Sasaoka | G02B 6/2551 385/95 |
| 6,766,720 B1 | 7/2004 | Jacobsen et al. | |
| 6,767,327 B1 | 7/2004 | Corl et al. | |
| 6,776,720 B2 | 8/2004 | Bartlett | |
| 6,908,442 B2 | 6/2005 | von Malmborg et al. | |
| 6,918,873 B1 | 7/2005 | Millar et al. | |
| 6,918,882 B2 | 7/2005 | Skujins et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,071,197 B2 | 7/2006 | Leonardi et al. | |
| 7,134,994 B2 | 11/2006 | Alpert et al. | |
| 7,162,926 B1 | 1/2007 | Guziak et al. | |
| 7,187,453 B2 | 3/2007 | Belleville | |
| 7,259,862 B2 | 8/2007 | Duplain et al. | |
| 7,265,847 B2 | 9/2007 | Duplain et al. | |
| 7,274,956 B2 | 9/2007 | Mott et al. | |
| 7,331,236 B2 | 2/2008 | Smith et al. | |
| 7,532,920 B1 | 5/2009 | Ainsworth | |
| 7,618,379 B2 | 11/2009 | Reynolds et al. | |
| 7,684,657 B2 | 3/2010 | Donlagic et al. | |
| 7,689,071 B2 | 3/2010 | Belleville et al. | |
| 7,715,903 B2 | 5/2010 | Hartley et al. | |
| 7,724,148 B2 | 5/2010 | Samuelsson et al. | |
| 7,731,664 B1 | 6/2010 | Millar | |
| 7,759,633 B2 | 7/2010 | Duplain et al. | |
| 7,783,338 B2 | 8/2010 | Ainsworth et al. | |
| 7,878,984 B2 | 2/2011 | Davis et al. | |
| 7,930,014 B2 | 4/2011 | Huenneckens et al. | |
| 7,946,997 B2 | 5/2011 | Hübinette | |
| 8,025,623 B1 | 9/2011 | Millar | |
| 8,029,447 B2 | 10/2011 | Kanz et al. | |
| 8,174,395 B2 | 5/2012 | Samuelsson et al. | |
| 8,216,151 B2 | 7/2012 | Smith | |
| 8,298,156 B2 | 10/2012 | Manstrom et al. | |
| 8,317,715 B2 | 11/2012 | Belleville et al. | |
| 8,343,076 B2 | 1/2013 | Sela et al. | |
| 8,410,940 B2 | 4/2013 | Samuelsson et al. | |
| 8,461,997 B2 | 6/2013 | Samuelsson et al. | |
| 8,485,985 B2 | 7/2013 | Manstrom et al. | |
| 8,555,712 B2 | 10/2013 | Narvaez et al. | |
| 8,556,820 B2 | 10/2013 | Alpert et al. | |
| 8,562,537 B2 | 10/2013 | Alpert et al. | |
| 8,583,218 B2 | 11/2013 | Eberle | |
| 8,636,659 B2 | 1/2014 | Alpert et al. | |
| 8,641,633 B2 | 2/2014 | Smith | |
| 8,641,639 B2 | 2/2014 | Manstrom et al. | |
| 8,676,299 B2 | 3/2014 | Schmitt et al. | |
| 8,698,638 B2 | 4/2014 | Samuelsson et al. | |
| 8,752,435 B2 | 6/2014 | Belleville et al. | |
| 8,936,401 B2 | 1/2015 | Belleville et al. | |
| 8,998,823 B2 | 4/2015 | Manstrom et al. | |
| 9,052,466 B2 | 6/2015 | Belleville et al. | |
| 2003/0069522 A1 | 4/2003 | Jacobsen et al. | |
| 2003/0180015 A1 * | 9/2003 | Yamamoto | G02B 6/2551 385/96 |
| 2004/0073141 A1 | 4/2004 | Hartley et al. | |
| 2004/0081404 A1 * | 4/2004 | Elliott | G02B 6/4457 385/55 |
| 2004/0181174 A2 | 9/2004 | Davis et al. | |
| 2005/0000294 A1 | 1/2005 | Tenerz et al. | |
| 2006/0122537 A1 | 6/2006 | Reynolds et al. | |
| 2008/0119758 A1 | 5/2008 | Samuelsson et al. | |
| 2009/0082678 A1 | 3/2009 | Smith | |
| 2009/0192412 A1 | 7/2009 | Sela et al. | |
| 2010/0145308 A1 | 6/2010 | Layman et al. | |
| 2010/0241008 A1 * | 9/2010 | Belleville | A61B 5/0215 600/478 |
| 2011/0046477 A1 * | 2/2011 | Hulvershorn | A61B 5/0215 600/424 |
| 2011/0071407 A1 | 3/2011 | Hulainette et al. | |
| 2011/0178413 A1 | 7/2011 | Schmitt et al. | |
| 2011/0186294 A1 | 8/2011 | Narvaez et al. | |
| 2011/0319773 A1 | 12/2011 | Kanz et al. | |
| 2012/0210797 A1 * | 8/2012 | Yu | G01L 9/0079 73/705 |
| 2012/0227505 A1 | 9/2012 | Belleville et al. | |
| 2012/0265102 A1 | 10/2012 | Leo et al. | |
| 2013/0051731 A1 * | 2/2013 | Belleville | G02B 6/3861 385/72 |
| 2013/0218032 A1 | 8/2013 | Belleville | |
| 2013/0296718 A1 | 11/2013 | Ranganathan et al. | |
| 2013/0317372 A1 | 11/2013 | Eberle et al. | |
| 2014/0005558 A1 | 1/2014 | Gregorich | |
| 2014/0058275 A1 | 2/2014 | Gregorich et al. | |
| 2014/0081244 A1 | 3/2014 | Voeller et al. | |
| 2014/0107624 A1 | 4/2014 | Belleville | |
| 2014/0121475 A1 | 5/2014 | Alpert et al. | |
| 2014/0241669 A1 | 8/2014 | Belleville et al. | |
| 2014/0248021 A1 | 9/2014 | Belleville et al. | |

FOREIGN PATENT DOCUMENTS

| | | |
|---|---|---|
| DE | 202014100938 U1 | 3/2014 |
| EP | 0235992 A1 | 9/1987 |
| EP | 0738495 A1 | 10/1996 |
| EP | 0879615 A1 | 11/1998 |
| EP | 0879617 A1 | 11/1998 |
| EP | 1039321 A2 | 9/2000 |
| EP | 1479407 A1 | 11/2004 |
| WO | 9313707 A1 | 7/1993 |
| WO | 9533983 A1 | 12/1995 |
| WO | 9945352 A1 | 9/1999 |
| WO | 2008034010 A2 | 3/2008 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2013033489 A1 | 3/2013 |
| WO | 2014025255 A1 | 2/2014 |

* cited by examiner

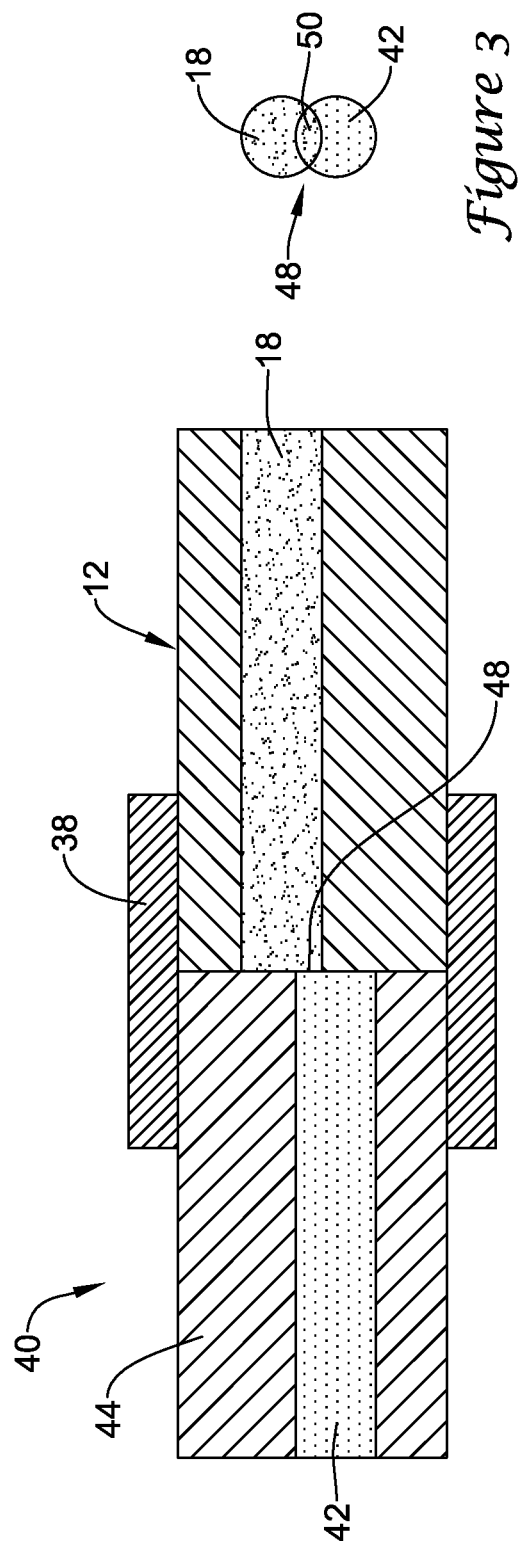

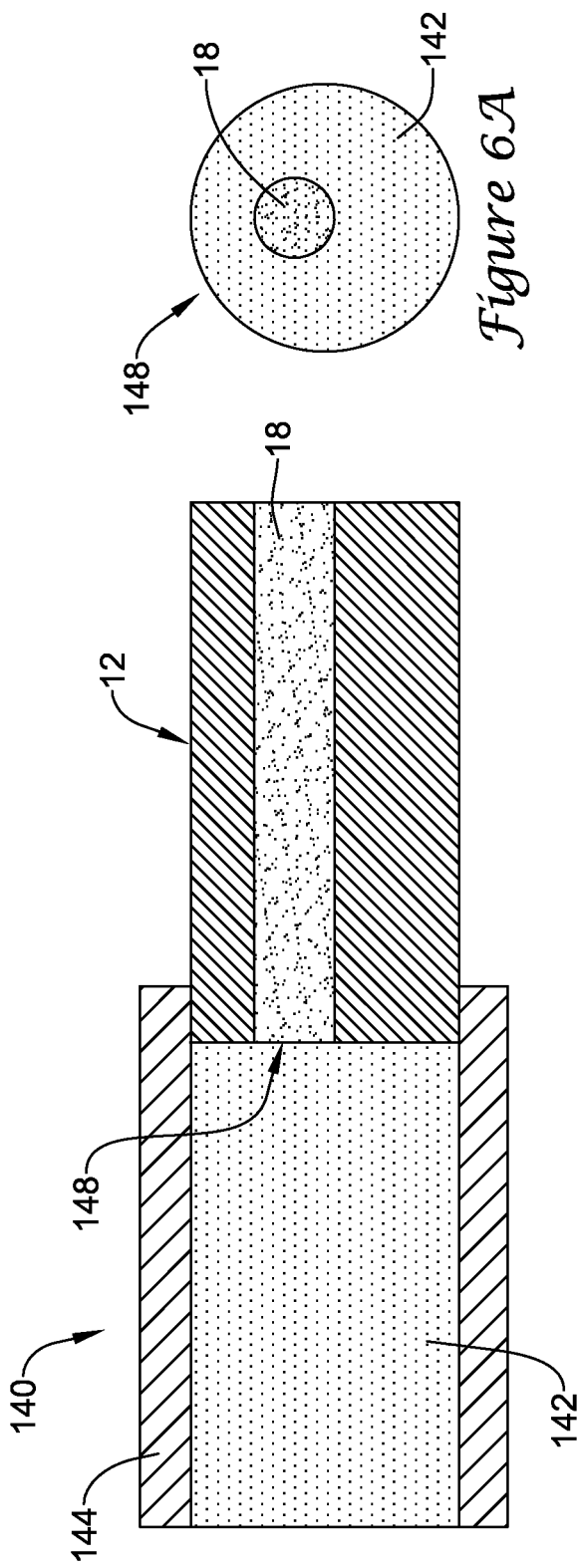
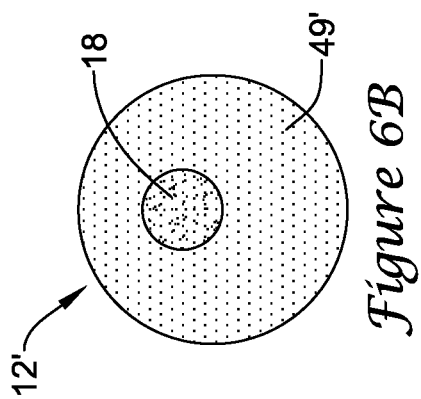
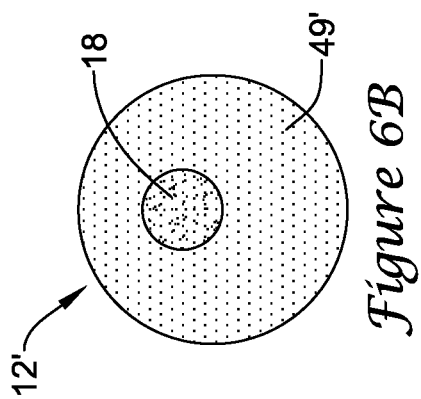
Figure 5
Figure 6A
Figure 6B

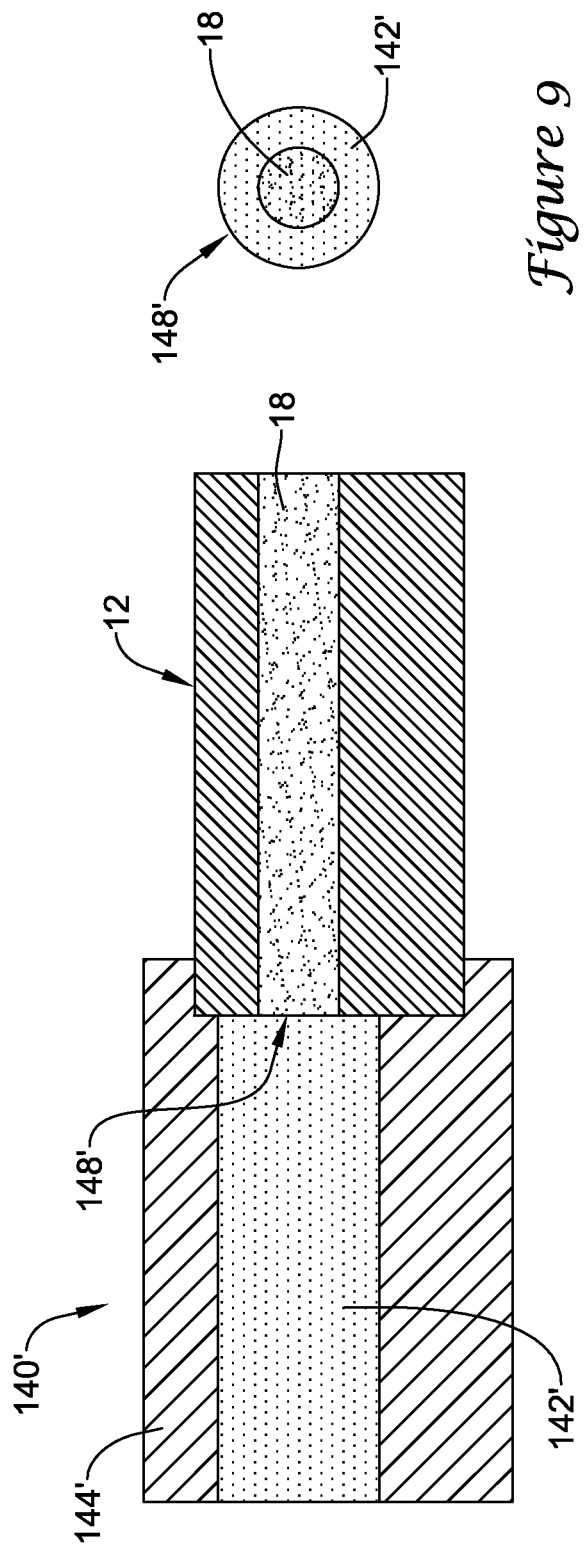

PRESSURE-SENSING MEDICAL DEVICES AND MEDICAL DEVICE SYSTEMS

CROSS-REFERENCE TO RELATED APPLICATIONS

This application claims priority under 35 U.S.C. § 119 to U.S. Provisional Application Ser. No. 61/693,625, filed Aug. 27, 2012, the entirety of which is incorporated herein by reference.

TECHNICAL FIELD

The present disclosure pertains to medical devices, and methods for manufacturing medical devices. More particularly, the present disclosure pertains pressure-sensing medical devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices and medical device systems. An example medical device system may include a guidewire. A pressure sensor assembly may be disposed within the guidewire. The pressure sensor assembly may include a pressure sensor and a first optical fiber coupled to the pressure sensor. The first optical fiber may have a first outer diameter. A cable may be coupled to the guidewire. The cable may include a second optical fiber. The second optical fiber may have a second outer diameter greater than the first outer diameter.

Another example medical device system may include a system for measuring blood pressure. The system may include a pressure-sensing guidewire. The pressure sensing guidewire may include an optical pressure sensor and a first optical fiber attached to the optical pressure sensor. The pressure-sensing guidewire may have a proximal end region having an outer diameter. An optical cable may be coupled to the pressure-sensing guidewire. The optical cable may include a second optical fiber having an outer diameter substantially equal to the outer diameter of the pressure-sensing guidewire.

A connector assembly for use with a pressure-sensing medical device is also disclosed. The connector assembly may include a connector body. A memory member may be coupled to the connector body. A first connector may be coupled to the connector body. The first connector may be configured to engage a pressure-sensing guidewire. A second connector may be coupled to the connector body. The second connector may be configured to engage an optical cable. A sleeve may be coupled to the connector body.

Another example medical device system for measuring blood pressure may include a pressure-sensing guidewire. The pressure sensing guidewire may include an optical pressure sensor and an optical fiber attached to the optical pressure sensor. An optical cable may be coupled to the pressure-sensing guidewire. The optical cable may be coupled to a control unit. A memory member may be coupled to the control unit. The memory member may include calibration data for the optical pressure sensor. The system may also include one or more identification members coupled to the pressure-sensing guidewire, the optical cable, or both. The one or more identification members may include an identifier that is configured to be matched with the calibration data for the optical pressure sensor.

Another example medical device system may include a guidewire. A pressure sensor assembly may be disposed within the guidewire. The pressure sensor assembly may include a pressure sensor and a first optical fiber coupled to the pressure sensor. The first optical fiber may have a first central core having a first outer diameter. A cable may be coupled to the guidewire. The cable may include a second optical fiber. The second optical fiber may have a second central core having a second outer diameter greater than the first outer diameter.

Another example medical device system may include a guidewire. A pressure sensor assembly may be disposed within the guidewire. The pressure sensor assembly may include a pressure sensor and a first optical fiber coupled to the pressure sensor. The first optical fiber may have a first mode field diameter (MFD). A cable may be coupled to the guidewire. The cable may include a second optical fiber. The second optical fiber may have a second MFD greater than the first MFD.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 2-3 are schematic illustrations depicting the misalignment of optical fibers;

FIG. 5 is a schematic illustration depicting the alignment and/or overlapping of optical fibers;

FIG. 6A is another schematic illustration depicting the alignment and/or overlapping of optical fibers;

FIG. 6B is an end view of an example guidewire;

FIGS. 8-9 are schematic illustrations depicting the alignment and/or overlapping of optical fibers;

Figure 1:
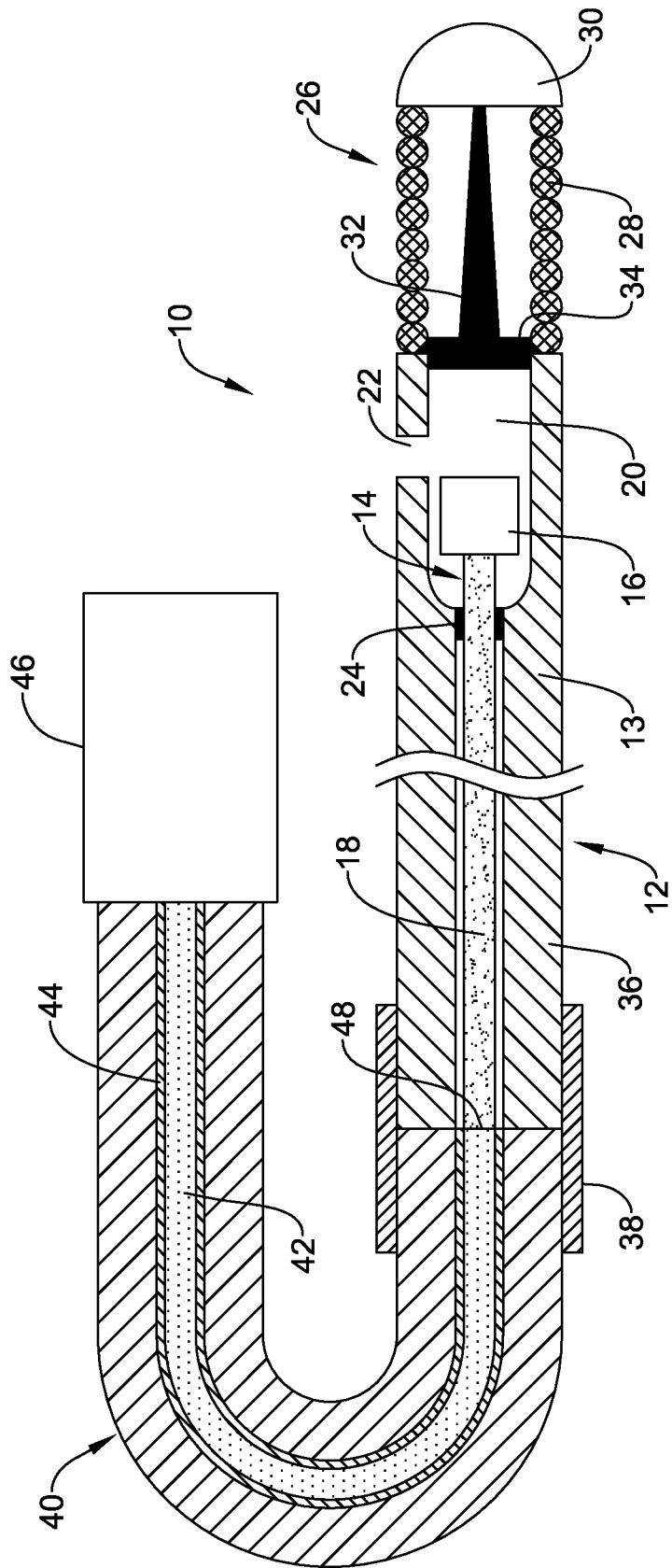
FIG. 1 is a partially cross-sectional side view of an example medical device system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis.

FIG. 1 is an example medical device system 10 that may be utilized to monitor blood pressure. System 10 may include a guidewire 12. In at least some embodiments, guidewire 12 may include a pressure-sensing (e.g., blood pressure sensing) guidewire. A pressure sensor or sensor assembly 14 may be disposed within guidewire 12 (e.g., within a tubular member or shaft portion 13 of guidewire 12). Sensor assembly 14 may include an optical pressure sensor 16 attached to an optical fiber 18. The form of pressure sensor 16 may vary. In at least some embodiments, pressure sensor 16 is a Fabry-Perot type pressure sensor. Pressure sensor 16 may be disposed within a housing region 20 of shaft portion 13 and generally adjacent to an opening 22 formed in shaft portion 13. Opening 22 may provide fluid access to pressure sensor 16. Optical fiber 18 may be bonded to shaft portion 13 at one or more locations such as, for example, at a bond 24.

Guidewire 12 may include a number of other structural features. For example, guidewire 12 may include a tip region 26. Tip region 26 may include a coil 28 and a tip member 30 (e.g., a solder ball tip member 30). A shaping member 32 may be disposed along tip region 26. Shaping member 32 may be bonded to shaft portion 13 and/or coil 28 at a bond 34. These are just examples. Other structures are contemplated for guidewire 12.

A proximal end region 36 of guidewire 12 may be attached to a connector 38. An optical cable 40 may also be attached or otherwise coupled to connector 38 at a position generally opposite of guidewire 12. Cable 40 may include a second optical fiber 42. A sheath or sleeve 44 may be disposed along fiber 42. Cable 40 may connect to additional devices such a control unit or signal conditioning unit 46, which, in turn, may connected to other devices such as electronics, displays, and the like.

At connector 38, fiber 18 and fiber 42 may come together at a joint or intersection point 48. At this point 48, signal may be communicated between fibers 18/42. When using optical cables and/or optical fibers, alignment of the optical fibers may be desirable. Even a slight misalignment of the optical fibers may lead to signal losses, which could skew, for example, communication between the fibers and may impact pressure measurements. When connecting fiber 18 and fiber 42 at connector 38, it is possible that the ends of fibers 18/42 may not precisely align. For example, FIGS. 2-3 schematically illustrate that when bringing together guidewire 12 and cable 40, fibers 18/42 may be slightly offset from one another at the intersection point 48. In doing so, only an overlapping portion 50 may communicate signal (e.g., light energy) in both directions without any losses while flanking portions of fibers 18/42 may not effectively communicate. Accordingly, when there is misalignment of fibers 18/42, there are losses at the intersection point 48 as the light travels in both directions (e.g., losses as the light travels from optical fiber 42 of optical cable 40 to optical fiber 18 of guidewire 12 and additional losses as the reflected light travels back from optical fiber 18 to optical fiber 42).

A number of approaches may be utilized to affect the precise alignment of the optical fibers. For example, it may be desirable to precisely align with optical fiber within the guidewire with the outer diameter of the guidewire. According to this embodiment, the optical cable may be designed to precisely align with the outer diameter of the guidewire and the known position of the optical fiber within the guidewire (e.g., centered) allows the optical fiber within the optical cable to be aligned therewith. While such an approach may be useful, it may be technically challenging and/or costly to implement.

Figure 4:
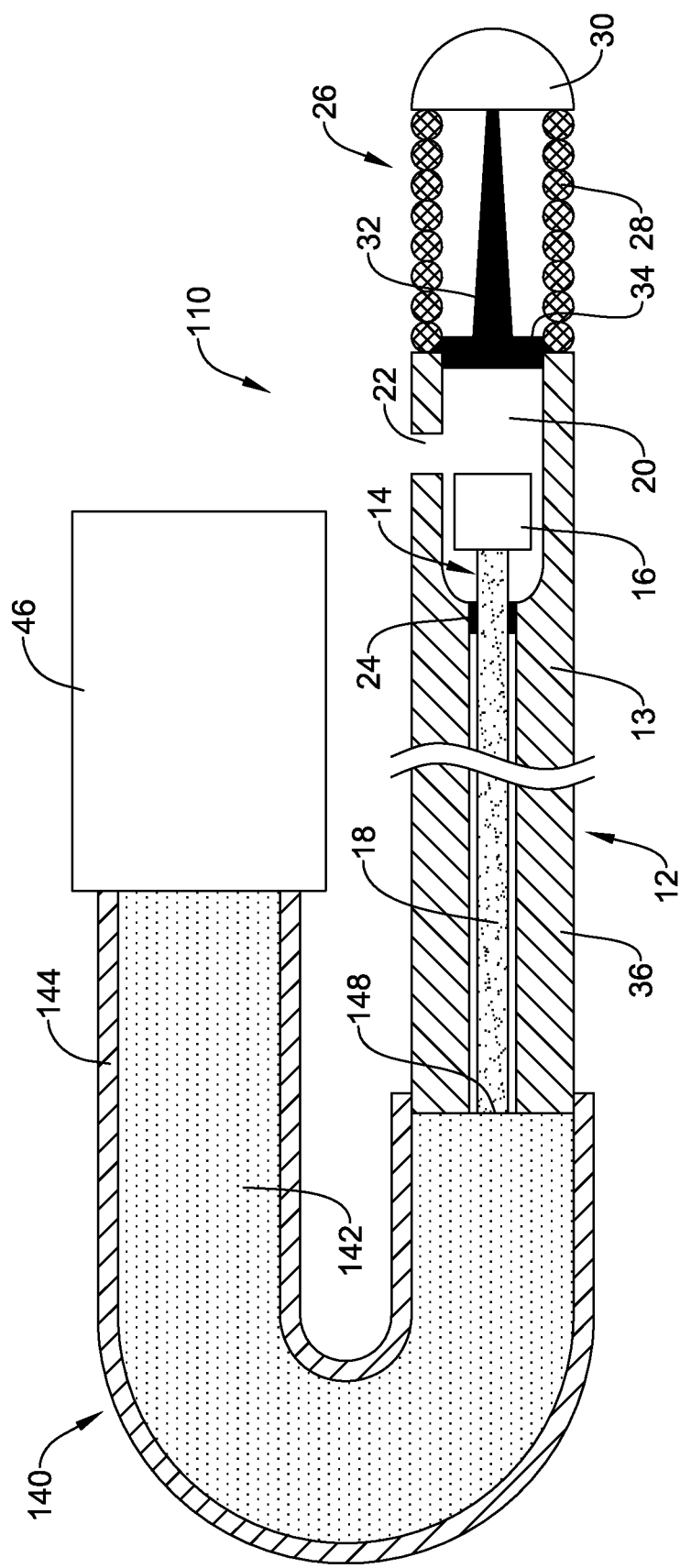
FIG. 4 is a partially cross-sectional side view of another example medical device system.

FIG. 4 illustrates another example system 110 that may be similar in form and function to other systems disclosed herein. In general, system 110 is designed to control for signal losses that may occur when attempting to align optical fibers. For example, system 110 may include cable 140 having optical fiber 142 disposed therein and sleeve 144. As shown in FIG. 4, guidewire 12 may be coupled to optical cable 140. This may include using a portion of sleeve 144 as a connector. Alternatively, a separate connector may be utilized. Some examples of using a separate connector are disclosed herein. It can be appreciated that a number of different structures/arrangements may be utilized to couple guidewire 12 with optical cable 140.

Optical fiber 142 is generally designed to be larger in diameter than fiber 18. In this example, optical fiber 142 may have an outer diameter that is substantially the same as the outer diameter of guidewire 12 (e.g., optical fiber 142 may have an outer diameter of about 0.014 inches or so when used with a 0.014 inch outer diameter guidewire). The precise diameter of optical fiber 142 may vary depending on the outer diameter of guidewire 12. However, the outer diameter of optical fiber 142 need not be exactly the same as the outer diameter of guidewire 12. For example, the outer diameter of optical fiber 142 may be slightly larger or slightly smaller than the outer diameter of guidewire 12. Having an outer diameter that approximates the outer diameter of guidewire 12 may ensure that fiber 142 is sufficiently large to completely cover the entire end surface of fiber 18 as shown in FIGS. 5-6A. Accordingly, essentially all signal transmitted to fiber 18 and then reflected back along optical fiber 18 is transmitted to optical fiber 142. Some signal transmitted distally along optical fiber 142 may be lost, but if the sizes of fibers 18/142 are known, system 110 can account for this "known" loss of signal.

While not explicitly shown in the drawings, it can be appreciated that optical fibers including fibers 18/142 generally include a central core or mode field and an outer jacket or cladding. For the purposes of this disclosure, the various optical fibers shown in the drawings may be understood to represent either the complete optical fiber (e.g., including the central core, outer cladding, and any other structure of the fiber) or just the central core or mode field of the fiber. In addition, the "outer diameter" of any of the various optical fibers disclosed herein may be understood to represent either the outer diameter of the complete optical fiber (e.g., including the central core, outer cladding, and any other structure of the fiber) or just the outer diameter of central core or mode field of the fiber (e.g., the "mode field diameter", MFD).

The outer diameter of fiber 142 (as described herein) may include both the central core and the outer cladding of fiber 142. It can be appreciated that if the outer diameter of fiber 142 (e.g., including the central core and the outer cladding) is substantially the same as the diameter of guidewire 12, the central core of fiber 142 would be at least somewhat smaller than the outer diameter of guidewire 12. However, in such a design the outer diameter of the central core of fiber 142 may still be larger than at least the outer diameter of the central core of fiber 18. This would allow the central core of fiber 142 to completely cover the central core of fiber 18. In some of these embodiments, the central core of fiber 142 may have an outer diameter that is the same as or larger than the outer diameter of the entire fiber 18 (e.g., including both the central core and outer cladding of fiber 18). In still other embodiments, the central core of fiber 142 may have an outer diameter that is substantially the same as the outer diameter of guidewire 12. These are just examples. Other sizes and/or configurations are contemplated.

In at least some embodiments, signal conditioning unit 46 may also include an optical fiber (not shown) that is designed to optically connect with optical fiber 142 (and/or optical fiber 18). The optical fiber within the signal conditioning unit 46 may have an outer diameter that is greater than the outer diameter of optical fiber 18 (e.g., the core of the optical fiber within the signal conditioning unit 46 may have a diameter that is greater than the core of optical fiber 18). In some embodiments, the outer diameter of the optical fiber within the signal conditioning unit 46 may be similar in size to the outer diameter of optical fiber 142. In other embodiments, the outer diameter of the optical fiber within the signal conditioning unit 46 may be larger than or smaller than the outer diameter of optical fiber 142. In one example, optical fiber 18 and optical fiber 142 may have a similar or the same outer diameter, and the outer diameter of the optical fiber within the signal conditioning unit 46 may be larger than the outer diameter of both optical fiber 18 and optical fiber 142. These are just examples.

FIG. 6B illustrates that guidewire 12' may include a coating 49' at its proximal end. Coating 49' may help to block surfaces of guidewire 12' that might otherwise allow for signal transmitted along fiber 142 to be reflected one or more times including surfaces other than optical fiber 18. This may help to reduce noise or otherwise help reduce unwanted/unaccounted for signal from fiber 142 from being transmitted to fiber 18. Coating 49' may be utilized with any of the guidewires disclosed herein.

The form of coating 49' may vary. For example, coating 49' may include an antireflective coating, an interference coating (e.g., silicon dioxide, magnesium oxide, magnesium fluoride, silica, or the like), an absorbing coating (e.g., titanium nitride, niobium nitride, or the like), combinations thereof, or the like. In some embodiments, portions of the proximal end of guidewire 12' may be textured so that coating 49' may be applied thereto. Alternatively, the texturing itself may define the "coating" and help to reduce unwanted reflections.

Figure 7:
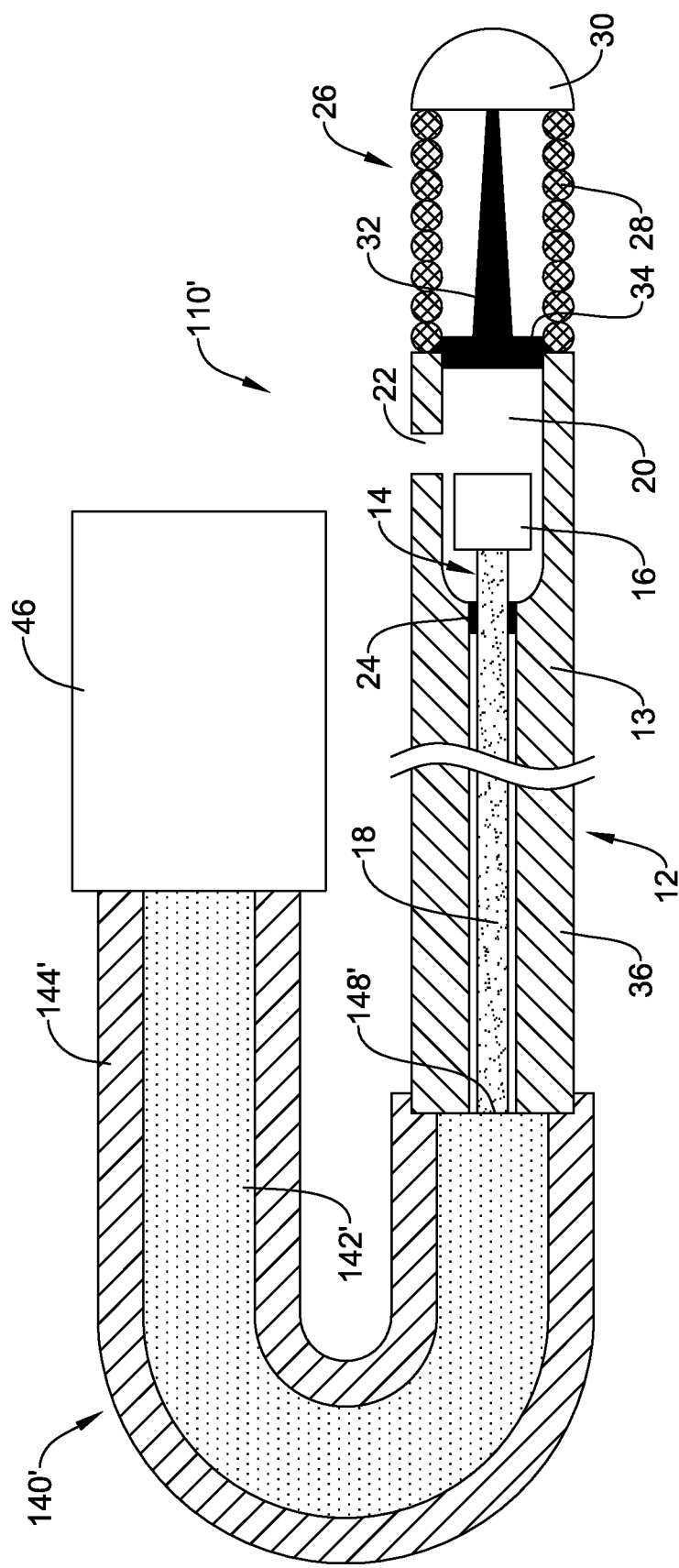
FIG. 7 is a partially cross-sectional side view of another example medical device system.

FIG. 7 illustrates another example system 110' that may be similar in form and function to other systems disclosed herein. System 110' may utilize cable 140'. Cable 140' may include an enlarged optical fiber 142' and sleeve 144'. Again, sleeve 144' may be used as a connector to aid in connecting optical cable 140' and guidewire 12 or a separate connector may be utilized. Optical fiber 142' is generally designed to be larger in diameter than fiber 18 (including having an outer diameter that is substantially the same as the outer diameter of guidewire 12 or otherwise being suitably sized as disclosed herein). This may allow fiber 142' to complete cover the entire surface of fiber 18 as shown in FIGS. 8-9. This may include sizing fiber 142' so that the MFD of fiber 142' completely covers the entire end surface of fiber 18 and/or the MFD of fiber 142' completely covers the MFD of fiber 18.

The diameter of fiber 142' may be smaller than fiber 142. In other words, fiber 142' need not have a diameter as large as the outer diameter of guidewire 12 and, instead, may be sized large enough so as to ensure coverage of fiber 18. In some of these and in other embodiments, fiber 142' may be sized so that the MFD of fiber 142' is larger than the MFD of fiber 18. This may include sizing fiber 142' so that outer diameter of fiber 142' (and/or the MFD of fiber 142') is at least 10% larger than fiber 18 (and/or the MFD of fiber 18), or so that outer diameter of fiber 142' (and/or the MFD of fiber 142') is at least 20% larger than fiber 18 (and/or the MFD of fiber 18), or so that outer diameter of fiber 142' (and/or the MFD of fiber 142') is at least 30% larger than fiber 18 (and/or the MFD of fiber 18) so that outer diameter of fiber 142' (and/or the MFD of fiber 142') is at least 40% larger than fiber 18 (and/or the MFD of fiber 18), or so that outer diameter of fiber 142' (and/or the MFD of fiber 142') is at least 50% larger than fiber 18 (and/or the MFD of fiber 18), or so that outer diameter of fiber 142' (and/or the MFD of fiber 142') is at least 60% larger than fiber 18 (and/or the MFD of fiber 18), or so that outer diameter of fiber 142' (and/or the MFD of fiber 142') is at least 70% larger than fiber 18 (and/or the MFD of fiber 18), or so that outer diameter of fiber 142' (and/or the MFD of fiber 142') is at least 80% larger than fiber 18 (and/or the MFD of fiber 18), or so that outer diameter of fiber 142' (and/or the MFD of fiber 142') is at least 90% larger than fiber 18 (and/or the MFD of fiber 18), or so that outer diameter of fiber 142' (and/or the MFD of fiber 142') is at least 100% larger than fiber 18 (and/or the MFD of fiber 18), These are just examples. Other sizes are contemplated.

Given that the manufacturing tolerances may be known for the positioning of fiber 18 within guidewire 12, fiber 142' may be designed to be large enough so that the end of fiber 142' can cover fiber 18 (e.g., large enough so the that end of the central of fiber 142' can cover the central core of fiber 18), taking into account manufacturing tolerances. For example, the process for manufacturing guidewire 12 may allow the positioning of fiber 18 within guidewire to be known within a certain distance. Taking into account these distances, fiber 142' (and/or the MFD of fiber 142') can be designed to be large enough to cover the end surface of fiber 18 (and/or the MFD of fiber 18), taking into account the known manufacturing tolerances.

Figure 10:
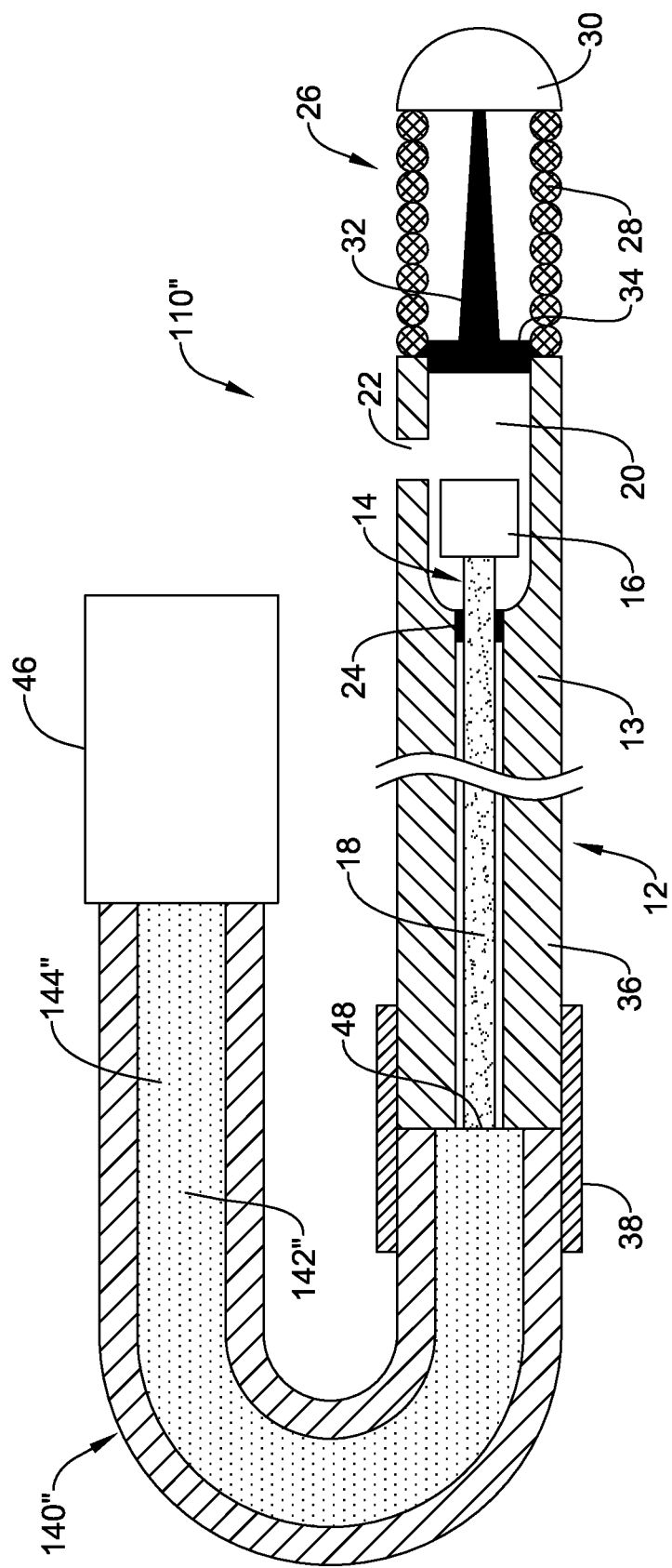
FIG. 10 is a partially cross-sectional side view of another example medical device system.

FIG. 10 illustrates another example system 110" that may be similar in form and function to other systems disclosed herein. System 110" may utilize cable 140". Cable 140" may include an enlarged optical fiber 142" and sleeve 144". Optical fiber 142" is generally designed to be larger in diameter than fiber 18 (including having an outer diameter that is substantially the same as the outer diameter of guidewire 12 or otherwise being suitably sized as disclosed herein). This may allow fiber 142" to completely cover the entire surface of fiber 18. This may include the central core or mode field of fiber 142" completely covering the entire surface of fiber 18 (and/or the central core of fiber 142" completely covering the central core or mode field of fiber 18). In at least some embodiments, fibers 18/142" may be joined at connector 38.

Figure 11:
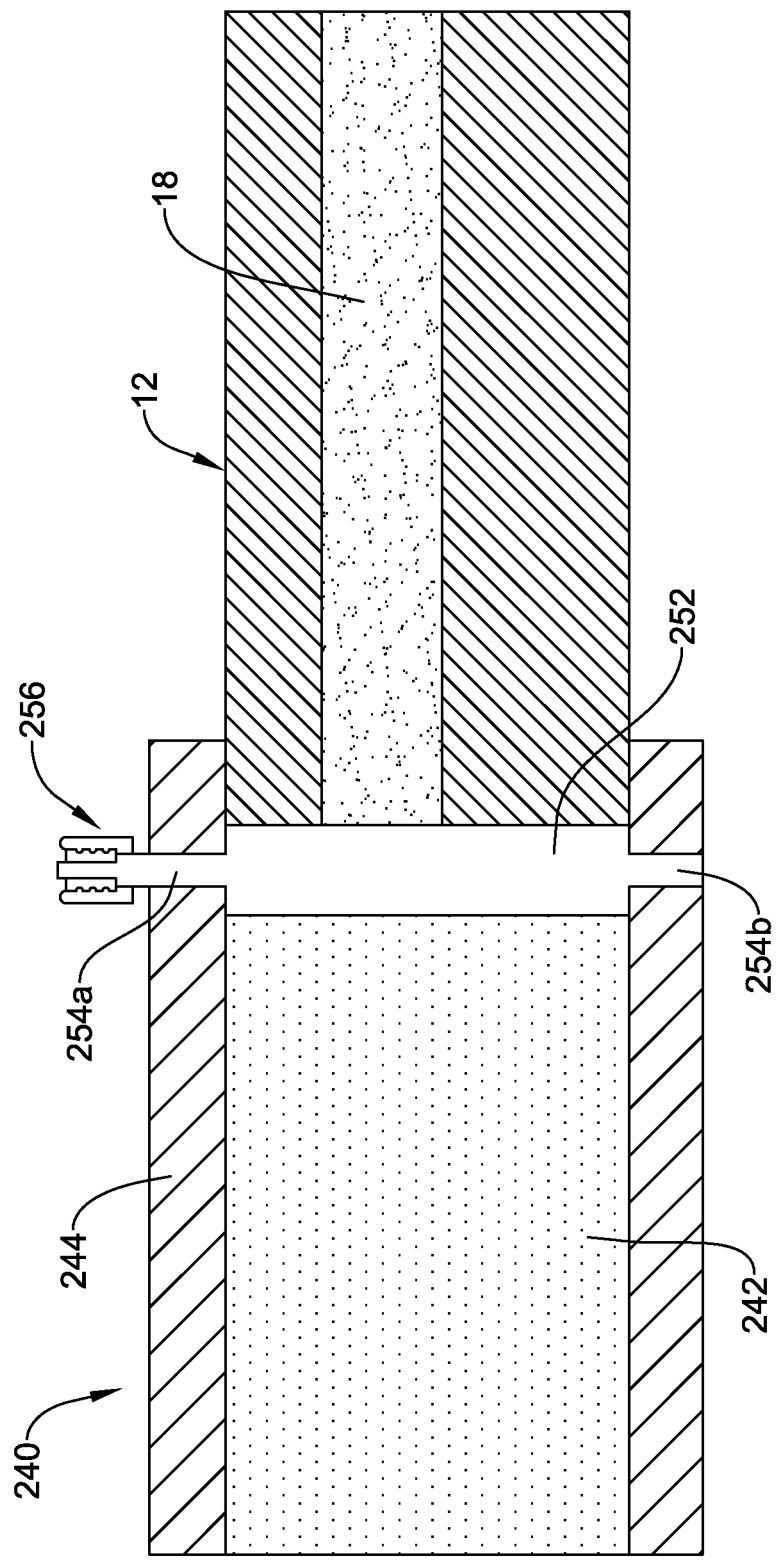
FIG. 11 is a partial cross-sectional side view of the intersection of an example guidewire and an example optical cable.

Sometimes the connection of an optical cable with a guidewire may leave a gap therebetween. In doing so, light may reflect within the gap, potentially leading to signal losses and/or noise. FIG. 11 illustrates cable 240 including optical fiber 242 and sleeve 244. Cable 240 may include one or more ports 254a/254b that are configured to allow fluid to be disposed within a gap 252 that may be present between cable 240 and guidewire 12 (e.g., between fibers 18/242). For example, fluid may be infused within the gap 252 via a fluid inlet connector 256 (e.g., a luer or other suitable connector). A syringe (not shown) may be connected to connector 256 and gap 252 may be flushed with fluid. The fluid may have a similar refractive index to silica (e.g., about 1.5) such as saline (e.g., which has a refractive index of about 1.35) so that reflective losses of signal can be reduced. In addition, the ability to flush gap 252 may allow blood or other opaque contaminants to be cleaned from the proximal surface of the guidewire 12.

Figure 11A:
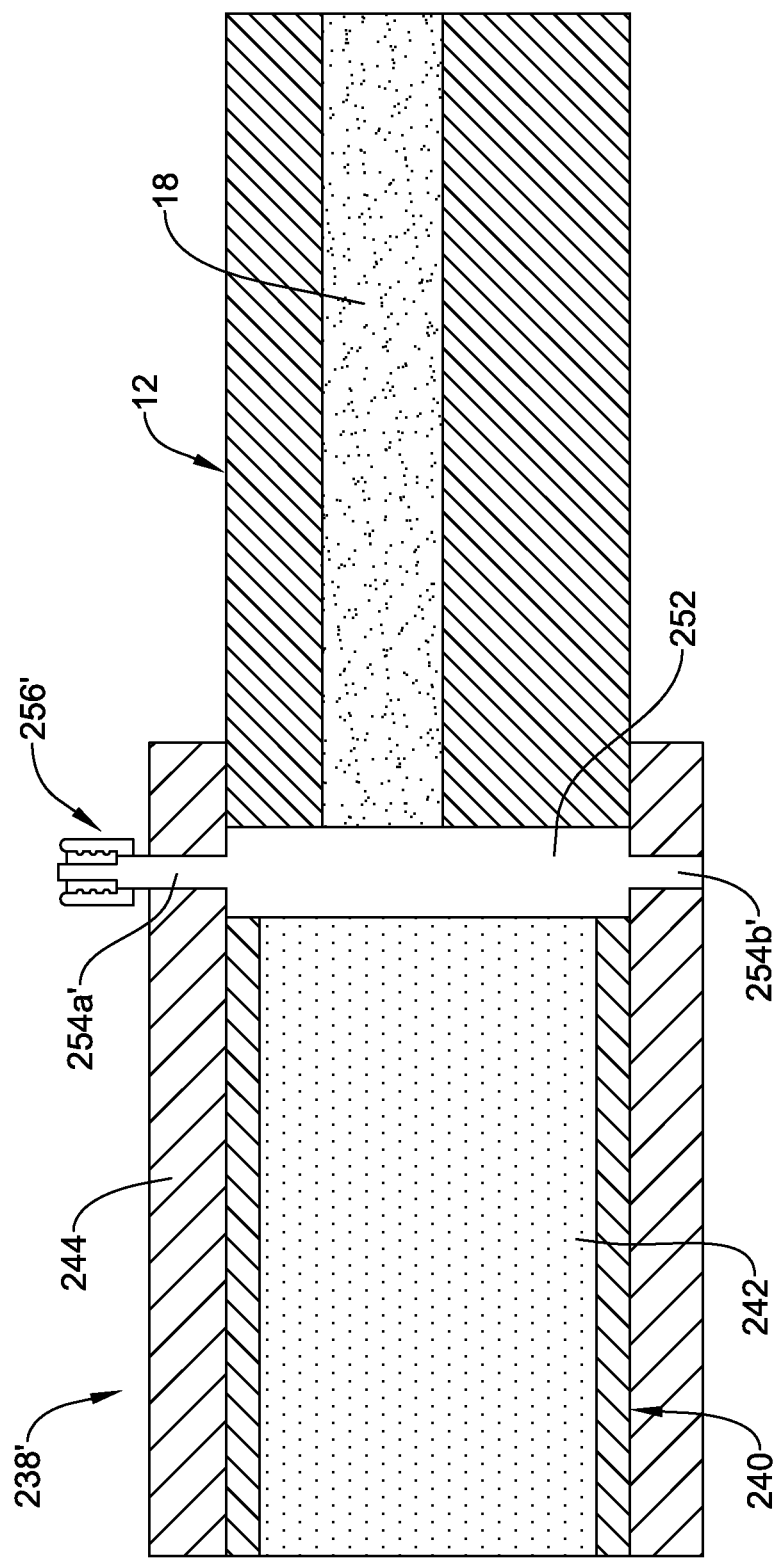
FIG. 11A is a partial cross-sectional side view of the intersection of an example guidewire and an example optical cable with a connector.

While FIG. 11 and the forgoing description indicate that cable 240 may include flushing capabilities, other arrangements are contemplated. For example, FIG. 11A illustrates that cable 240 and guidewire 12 may be coupled using connector 238' having flushing capabilities. Accordingly, connector 238' may have ports 254a'/254b' and fluid inlet connector 256'. Fluid may be infused within gap 252 via connector 238' and/or ports 254a'/254b'.

Figure 12:
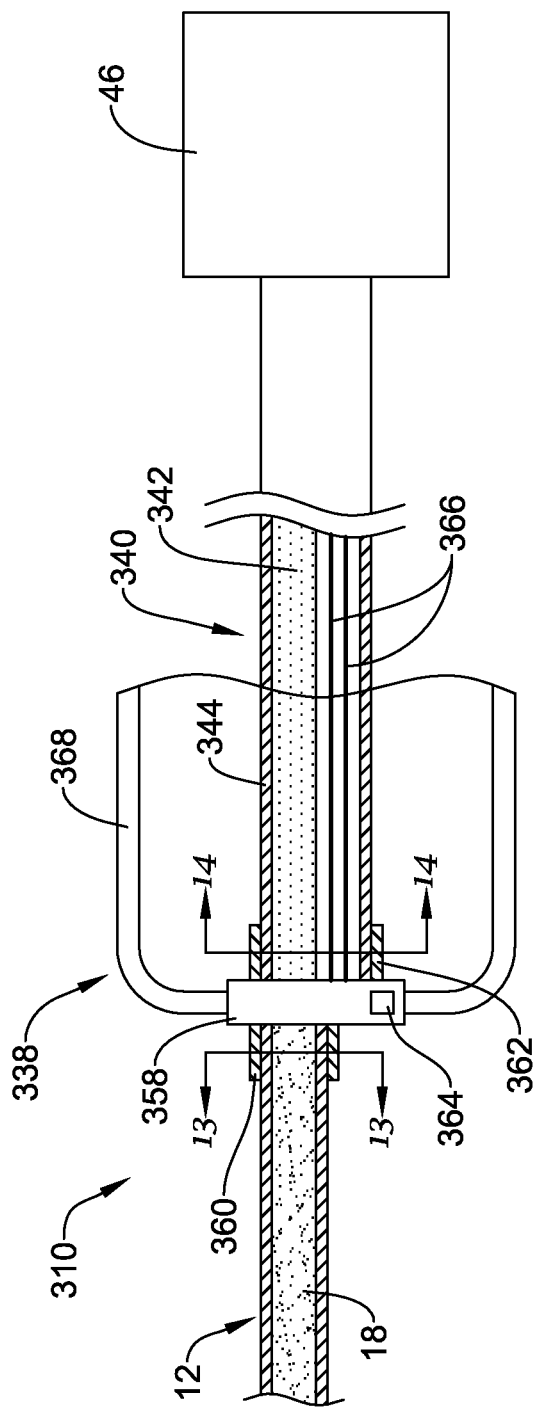
FIG. 12 is a partially cross-sectional side view of a portion of another example medical device system.
Figure 14:
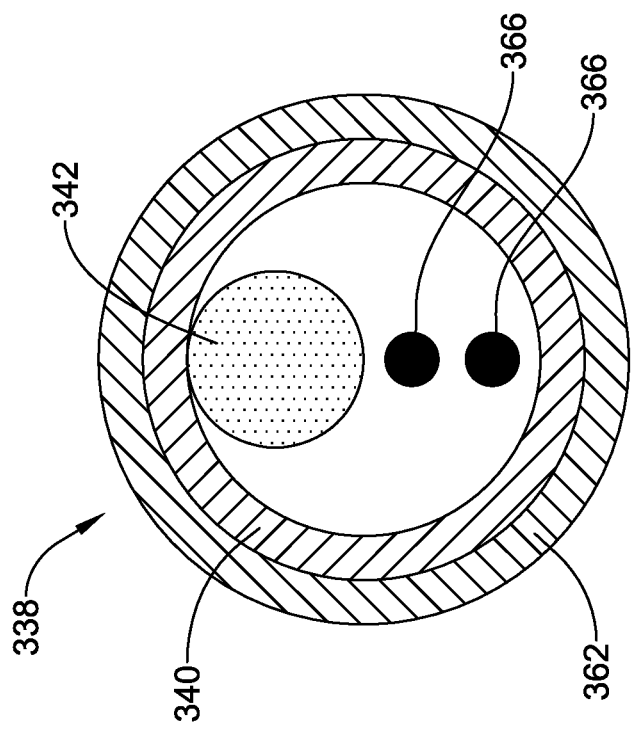
FIG. 14 is a cross-sectional view taken through line 14-14 in FIG. 12.
Figure 13:
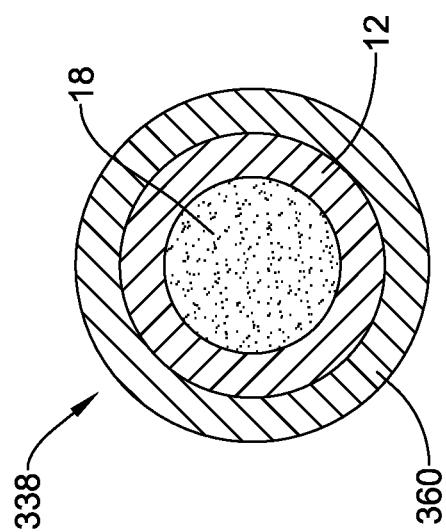
FIG. 13 is a cross-sectional view taken through line 13-13 in FIG. 12.

FIG. 12 illustrates another example system 310 that may be similar in form and function to other systems disclosed herein. System 310 may include connector assembly 338. Connector assembly 338 may include a housing or body 358. In at least some embodiments, body 358 may be generally disk-shaped. Other shapes are contemplated. A first connector 360 may be coupled to body 358. In general, connector 360 may be configured to connect with guidewire 12 as shown in FIGS. 12-13. A second connector 362 may also be coupled to body 358. Connector 362 may be generally configured to connect with optical cable 342 (which may include optical fiber 342 and cable sleeve 344) as shown in FIGS. 12 and 14. Connectors 360/362 may be arranged in a suitable configuration. In at least some embodiments, connectors 360/362 may be arranged "back-to-back".

Body 358 may also include a memory member 364. Memory member 364 may include a suitable memory chip or storage medium such as, for example, a PROM, EPROM, EEPOM, ROM, flash memory, solid state memory, or the like. Memory member 364 may be integral with body 358 or memory member 364 may be removably coupled to body 358. In general, memory member 364 may store calibration data specific to the sensor (e.g., sensor 16) on guidewire 12. This may allow a user to form an appropriate calibration curve unique to sensor 16 so that accurate pressure measurements may be performed. One or more wires 366 may attach to body 358 and may be utilized to communicate the calibration data to a suitable second device such as, for example, control unit or signal conditioning unit 46.

Connector assembly 338 may also include a sleeve 368. Sleeve 368 may be configured to be rolled back over a portion of cable 340. Such an arrangement may be desirable for a number of reasons. For example, guidewire 12 may be disposed within a sterile field during an intervention. Optical cable 340, in contrast, may be positioned outside the sterile field. It may be desirable to move portions of system 310 (e.g., guidewire 12 and/or optical cable 340) during the intervention. Because optical cable 340 may be positioned outside the sterile field, movements that would position optical cable 340 nearer or within the sterile field may not be desirable. Sleeve 368 may allow some movement of cable 340 relative to the sterile field. For example, sleeve 368 may be positioned within the sterile field and rolled back onto a portion of cable 340, thereby covering a portion of cable 340 and allowing that portion to be moved into the sterile field.

Figure 15:
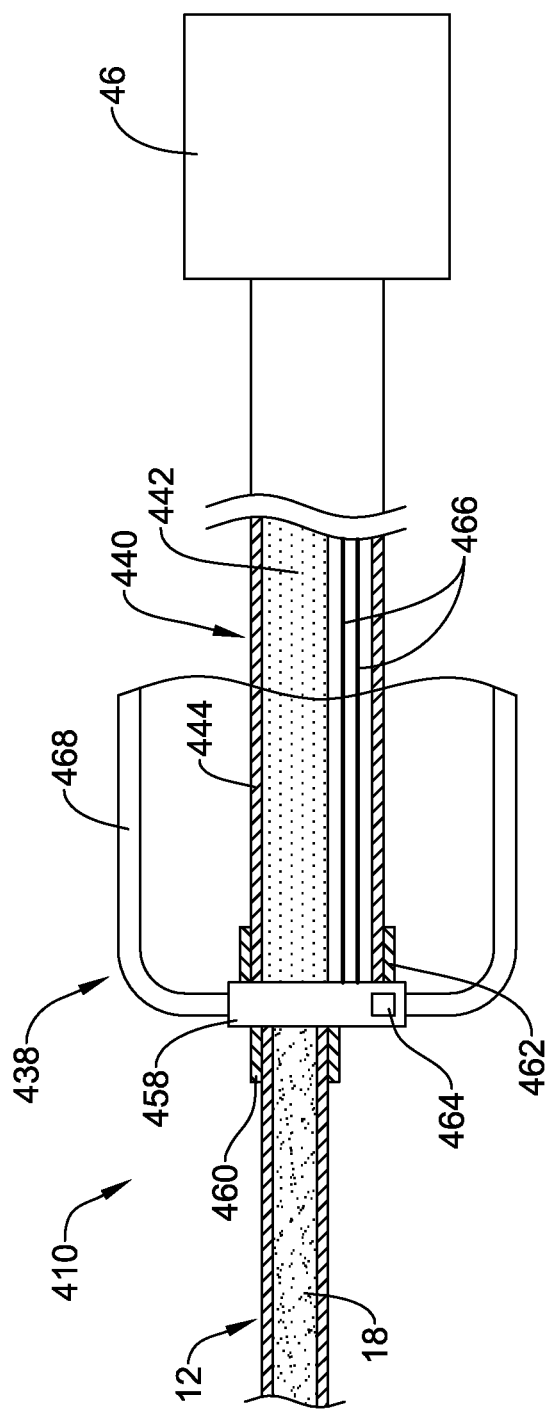
FIG. 15 is a partially cross-sectional side view of a portion of another example medical device system.

FIG. 15 illustrates another example system 410 that may be similar in form and function to other systems disclosed herein. System 410 may include connector assembly 438. Connector assembly 438 may include a housing or body 458. First connector 460 may be coupled to body 458 and may be configured to connect with guidewire 12. Second connector 462 may also be coupled to body 458 and may be generally configured to connect with optical cable 440 (which may include optical fiber 442 and cable sleeve 444). Body 458 may also include a memory member 464. In general, memory member 464 may store calibration data specific to the sensor (e.g., sensor 16) on guidewire 12. One or more wires 466 may attach to body 458 and may be utilized to communicate the calibration data to a suitable second device such as, for example, signal conditioning unit 46. Connector assembly 438 may also include a sleeve 468.

According to this embodiment, optical cable 440 may utilize optical fiber 442 that is sized to be larger than optical fiber 18 much like other "enlarged" optical fibers disclosed herein (including having an outer diameter that is substantially the same as the outer diameter of guidewire 12 or otherwise being suitably sized as disclosed herein). In doing so, signal losses and/or noise may be reduced.

Figure 16:
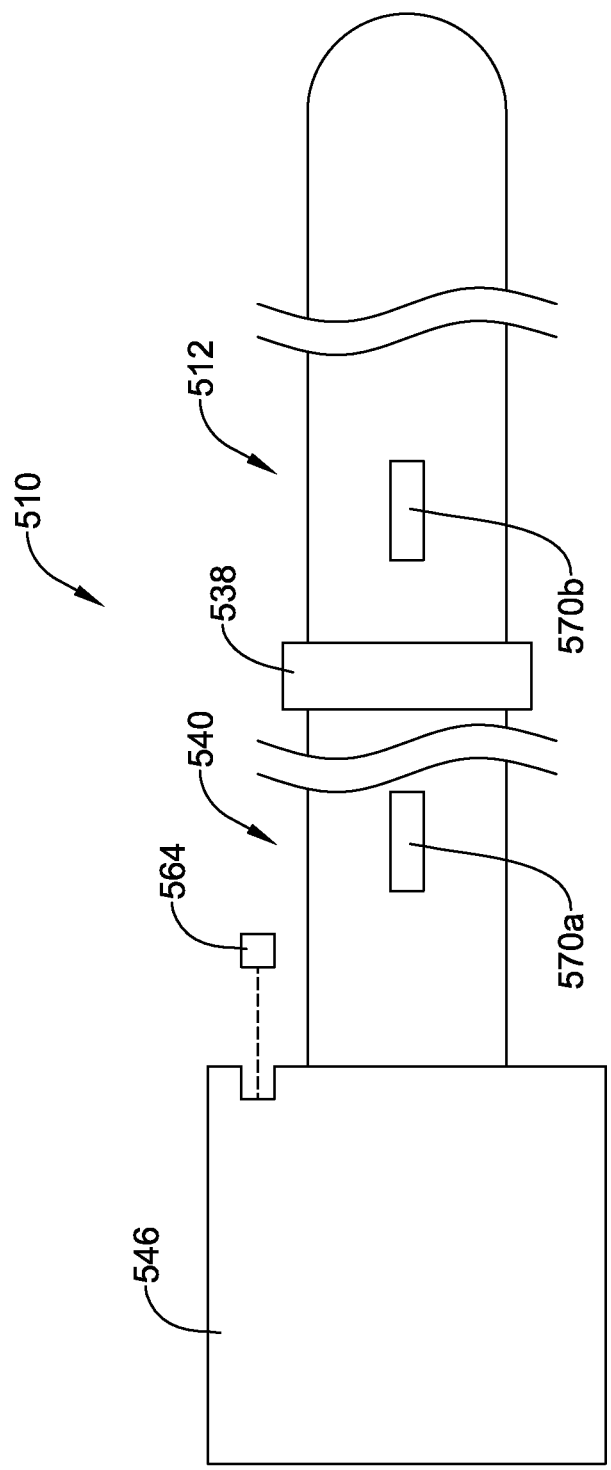
FIG. 16 is a partially cross-sectional side view of another example medical device system.

FIG. 16 illustrates another example system 510 that may be similar in form and function to other systems disclosed herein. System 510 may include guidewire 512 and optical cable 540. Guidewire 512 and cable 540 may be coupled to one another with a connector 538. System 510 may also have a control unit or signal conditioning unit 546. Unit 546 may be configured to receive memory member 564, which may include calibration data for a sensor (e.g., sensor 16) on guidewire 512. For example, unit 546 may include a port or slot for receiving memory member 564.

Calibration data for optical pressure sensors are generally specific to a particular sensor. When memory chips containing calibration data for an optical pressure sensor are utilized with a control unit, it is possible that a clinician may fail to remove an "old" memory chip (utilized in conjunction with a different pressure sensor during a past intervention) from the control unit and may proceed to use the "old" calibration data with subsequent pressure sensors. This may continue for a number of different procedures. Because the calibration data is generally specific to a particular pressure sensor/wire, "reusing" calibration data for an "old" pressure sensor in a "new" intervention may lead to incorrect pressure readings.

System 510 is designed to help increase the possibility that the correct calibration data is utilized with the corresponding pressure sensor. For example, cable 540 may include an identification member 570a. Identification member 570a may generally include a unique identifier that can be matched with memory member 564. A portion of system 510 may require that proper matching of identification member 570a with memory member 564 occurs prior to performing an intervention. For example, control unit 546 may require some affirmation that identification member 570a and memory member 564 are matched before signals can be sent to/from control unit 546. For example, identification member 570a may take the form of a unique identification number printed on cable 540. A user may input the identification number into control unit 546. If the identification number is properly matched with memory member 564 (e.g., if the memory member 564 contains a matching identification number or otherwise can be utilized to recognize the proper, matching identification number), control unit 546 may be allowed to be used for the intervention. If the identification number does not match, a user may be alerted to this "mismatch" so that the proper memory member 564 can be utilized.

In at least some embodiments, identification member 570a may include only a unique identifier that can be matched with a corresponding memory member 564 and does not, itself, include any calibration data for an optical pressure sensor. Only the memory member 564 may include the calibration data and matching with the corresponding identification member 570a helps to insure the proper calibration data is utilized with corresponding pressure sensor.

The form of identification member 570a may vary. For example, identification member 570a may include a bar code, one or more numbers and/or letters, an image, or other identifier. The identification member 570a may be matched by inputting identification member 570a into, for example, control unit 546. For example, if identification member 570a is a bar code, a bar code scanner may be used to scan the bar code. The control unit 546 may receive the scanned bar code and attempt to match it with the calibration data contained on memory member 564. Alternatively, if identification member 570a includes one or more numbers and/or letters, a user may directly input the numbers/letters into the control unit 546 for matching with memory member 564. Other configurations and/or processes may be utilized to match identification member 570a with memory member 564.

The position of identification member 570a may vary. For example, identification member 570a may be positioned on cable 540. In addition or in the alternative, another identification member 570b may also be positioned on guidewire 512.

The materials that can be used for the various components of system 10 (and/or other systems disclosed herein) may include those commonly associated with medical devices. For simplicity purposes, the following discussion makes reference to guidewire 12. However, this is not intended to limit the devices and methods described herein, as the discussion may be applied to other similar devices and/or components of devices disclosed herein.

Guidewire 12 and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEV-LAR®), polysulfone, nylon, nylon-12 (such as GRIL-AMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of guidewire 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 12 to achieve the same result.

In some embodiments, a degree of Magnetic Resonance Imaging (MRI) compatibility is imparted into guidewire 12. For example, guidewire 12 or portions thereof may be made of a material that does not substantially distort the image and create substantial artifacts (i.e., gaps in the image). Certain ferromagnetic materials, for example, may not be suitable because they may create artifacts in an MRI image. Guidewire 12 or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

As alluded to above, guidewire 12 may include shaft portion 13. In some embodiments, shaft portion 13 may include one or more tubular members that may have slots formed therein. Various embodiments of arrangements and configurations of slots are contemplated. For example, in some embodiments, at least some, if not all of the slots are disposed at the same or a similar angle with respect to the longitudinal axis of shaft portion 13. As shown, the slots can be disposed at an angle that is perpendicular, or substantially perpendicular, and/or can be characterized as being disposed in a plane that is normal to the longitudinal axis of shaft portion 13. However, in other embodiments, the slots can be disposed at an angle that is not perpendicular, and/or can be characterized as being disposed in a plane that is not normal to the longitudinal axis of shaft portion 13. Additionally, a group of one or more the slots may be disposed at different angles relative to another group of one or more the slots. The distribution and/or configuration of the slots can also include, to the extent applicable, any of those disclosed in U.S. Pat. Publication No. US 2004/0181174, the entire disclosure of which is herein incorporated by reference.

The slots may be provided to enhance the flexibility of shaft portion 13 while still allowing for suitable torque transmission characteristics. The slots may be formed such that one or more rings and/or tube segments interconnected by one or more segments and/or beams that are formed in shaft portion 13, and such tube segments and beams may include portions of shaft portion 13 that remain after the slots are formed in the body of shaft portion 13. Such an interconnected structure may act to maintain a relatively high degree of torsional stiffness, while maintaining a desired level of lateral flexibility. In some embodiments, some adjacent the slots can be formed such that they include portions that overlap with each other about the circumference of shaft portion 13. In other embodiments, some adjacent the slots can be disposed such that they do not necessarily overlap with each other, but are disposed in a pattern that provides the desired degree of lateral flexibility.

Additionally, the slots can be arranged along the length of, or about the circumference of, shaft portion 13 to achieve desired properties. For example, adjacent the slots, or groups of the slots, can be arranged in a symmetrical pattern, such as being disposed essentially equally on opposite sides about the circumference of shaft portion 13, or can be rotated by an angle relative to each other about the axis of shaft portion 13. Additionally, adjacent the slots, or groups of the slots, may be equally spaced along the length of shaft portion 13, or can be arranged in an increasing or decreasing density pattern, or can be arranged in a non-symmetric or irregular pattern. Other characteristics, such as slot size, slot shape, and/or slot angle with respect to the longitudinal axis of shaft portion 13, can also be varied along the length of shaft portion 13 in order to vary the flexibility or other properties. In other embodiments, moreover, it is contemplated that the portions of the tubular member, such as a proximal section, or a distal section, or the entire shaft portion 13, may not include any such the slots.

As suggested herein, the slots may be formed in groups of two, three, four, five, or more the slots, which may be located at substantially the same location along the axis of shaft portion 13. Alternatively, a single slot may be disposed at some or all of these locations. Within the groups of the slots, there may be included the slots that are equal in size (i.e., span the same circumferential distance around shaft portion 13). In some of these as well as other embodiments, at least some the slots in a group are unequal in size (i.e., span a different circumferential distance around shaft portion 13). Longitudinally adjacent groups of the slots may have the same or different configurations. For example, some embodiments of shaft portion 13 include the slots that are equal in size in a first group and then unequally sized in an adjacent group. It can be appreciated that in groups that have two the slots that are equal in size and are symmetrically disposed around the tube circumference, the centroid of the pair of beams (i.e., the portion of shaft portion 13 remaining after the slots are formed therein) is coincident with the central axis of shaft portion 13. Conversely, in groups that have two the slots that are unequal in size and whose centroids are directly opposed on the tube circumference, the centroid of the pair of beams can be offset from the central axis of shaft portion 13. Some embodiments of shaft portion 13 include only slot groups with centroids that are coincident with the central axis of the shaft portion 13, only slot groups with centroids that are offset from the central axis of shaft portion 13, or slot groups with centroids that are coincident with the central axis of shaft portion 13 in a first group and offset from the central axis of shaft portion 13 in another group. The amount of offset may vary depending on the depth (or length) of the slots and can include other suitable distances.

The slots can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the shaft portion 13 is formed by cutting and/or removing portions of the tube to form the slots. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 12 may include forming the slots in shaft portion 13 using these or other manufacturing steps.

In at least some embodiments, the slots may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow shaft portion 13 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form shaft portion 13 without being limited by a minimum cutting blade size. Consequently, shaft portion 13 may be fabricated for use in neurological devices or other devices where a relatively small size may be desired.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
    a guidewire;
    a pressure sensor assembly disposed within the guidewire, the pressure sensor assembly including a pressure sensor and a first optical fiber coupled to the pressure sensor;
    wherein the first optical fiber has a first core having a first core diameter, a first cladding disposed about the first core, and a first outer diameter;
    wherein the first outer diameter of the first optical fiber is defined by an outer diameter of the first cladding;
    a cable coupled to the guidewire, the cable including a second optical fiber; and
    wherein the second optical fiber has a second core having a second core diameter greater than the first core diameter, a second cladding disposed about the second core, and a second outer diameter defined by an outer diameter of the second cladding, wherein the second outer diameter is equal to the first outer diameter.

2. The medical device system of claim 1, wherein the guidewire has an outer diameter and wherein the cable has a cable outer diameter that is equal to or greater than the outer diameter of the guidewire.

3. The medical device system of claim 1, wherein the cable includes a port for infusing fluid adjacent an intersection point between the cable and the guidewire.

4. The medical device system of claim 1, wherein the cable is coupled to the guidewire by a connector.

5. The medical device system of claim 4, wherein the connector includes a port for infusing fluid within the connector adjacent an intersection point between the cable and the guidewire.

6. The medical device system of claim 4, wherein the connector includes a guidewire connector configured to engage the guidewire and a cable connector configured to engage the cable.

7. The medical device system of claim 4, wherein the connector includes a body having a memory member coupled thereto.

8. The medical device system of claim 7, wherein the memory member includes calibration data for the pressure sensor.

9. The medical device system of claim 8, wherein the cable includes one or more wires that are configured to transmit the calibration data to a signal conditioning unit.

10. The medical device system of claim 4, wherein the connector includes a sleeve that is configured to be disposed about a portion of the cable.

11. The medical device system of claim 1, wherein the cable is coupled to a signal conditioning unit.

12. The medical device system of claim 1, wherein the guidewire has a proximal end including an anti-reflective coating.

13. A medical device system, comprising:
a guidewire;
a pressure sensor assembly disposed within the guidewire, the pressure sensor assembly including a pressure sensor and a first optical fiber coupled to the pressure sensor;
wherein the first optical fiber has a first central core having a first core outer diameter, and wherein the first optical fiber has a first cladding defining a first fiber outer diameter;
a cable coupled to the guidewire, the cable including a second optical fiber; and
wherein the second optical fiber has a second central core having a second core outer diameter greater than the first core outer diameter, and wherein the second optical fiber has a second cladding defining a second fiber outer diameter; and
wherein the first fiber outer diameter and the second fiber outer diameter are the same.

14. A medical device system, comprising:
a guidewire;
a pressure sensor assembly disposed within the guidewire, the pressure sensor assembly including a pressure sensor and a first optical fiber coupled to the pressure sensor;
wherein the first optical fiber includes a first core having a first core diameter;
wherein the first optical fiber includes a first cladding having a first cladding diameter;
a cable coupled to the guidewire, the cable including a second optical fiber;
wherein the second optical fiber includes a second core having a second core diameter greater than the first core diameter; and
wherein the second optical fiber includes a second cladding having a second cladding diameter equal to the first cladding diameter.

* * * * *